United States Patent [19]

Sarholz

[11] 4,307,061

[45] Dec. 22, 1981

[54] SELF-RECOVERING SOOT DETECTOR, PARTICULARLY TO MONITOR CARBON CONTENT IN DIESEL ENGINE EXHAUST GASES

[75] Inventor: Walter Sarholz, Stuttgart, Fed. Rep. of Germany

[73] Assignee: Robert Bosch GmbH, Stuttgart, Fed. Rep. of Germany

[21] Appl. No.: 62,361

[22] Filed: Jul. 31, 1979

[30] Foreign Application Priority Data

Aug. 17, 1978 [DE] Fed. Rep. of Germany ....... 2836002

[51] Int. Cl.³ .................... G01N 27/04; H01C 1/00; H01T 13/14
[52] U.S. Cl. ........................ 422/94; 60/276; 313/118; 313/130; 422/97; 422/98
[58] Field of Search ............ 422/97, 98, 119, 90, 422/94; 338/34; 60/276; 123/119 EL; 324/71 SN; 313/118, 127, 130, 131 R, 131 A, 132, 138, 141, 142

[56] References Cited

U.S. PATENT DOCUMENTS

| | | | |
|---|---|---|---|
| 2,128,457 | 8/1938 | Fairchild | 313/127 |
| 3,442,693 | 5/1969 | Rea | 313/131 R |
| 3,695,848 | 10/1972 | Taguchi | 324/71 SN |
| 4,039,941 | 8/1977 | Morrison | 338/34 |
| 4,066,413 | 1/1978 | Segawa et al. | 422/98 |
| 4,130,797 | 12/1978 | Hattoic et al. | 422/98 |
| 4,158,610 | 6/1979 | Bauer | 422/119 |

FOREIGN PATENT DOCUMENTS 745016 2/1956 United Kingdom ........... 313/131 A

Primary Examiner—Michael S. Marcus
Attorney, Agent, or Firm—Frishauf, Holtz, Goodman & Woodward

[57] ABSTRACT

An insulating support body, for example an aluminum oxide ceramic, supports two electrodes spaced from each other by a small gap, for example 0.1 mm, which will have therebetween a high resistance. Upon collection of soot, the resistance between the electrodes across the gap will drop, which can be indicated by sensing current through the electrodes upon connection to a source of electrical energy. To remove soot upon termination of smoking, or soot contents in the gases, the electrodes are applied over, or embedded in a layer of essentially non-conducting catalyzing material which, in the presence of oxygen, catalyzes the oxidation of soot located in the gap between the electrodes to thereby remove the soot by oxidation and restore the resistance of the path between the electrodes and hence the sensitivity of the sensor for subsequent detection of accumulation of soot in the gap. Preferably, the non-conductive catalyzing material is a mixture of platinum, or a platinum metal, or a platinum metal alloy and a metal oxide which is compatible with, or identical to the ceramic base, for example aluminum oxide. The essentially electrically non-conductive layer can be applied by thick-film technology, and the electrodes also by thick-film technology thereover, or the electrodes may be in the form of fine platinum wires extending through the catalyzing electrically non-conductive layer. The sensing element can be held in a housing or socket, similar to a spark plug socket.

14 Claims, 3 Drawing Figures

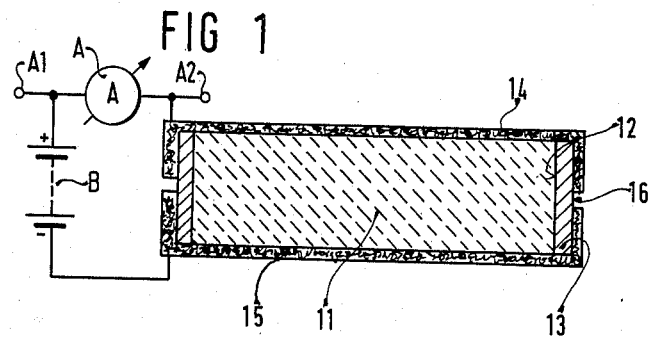
FIG 1
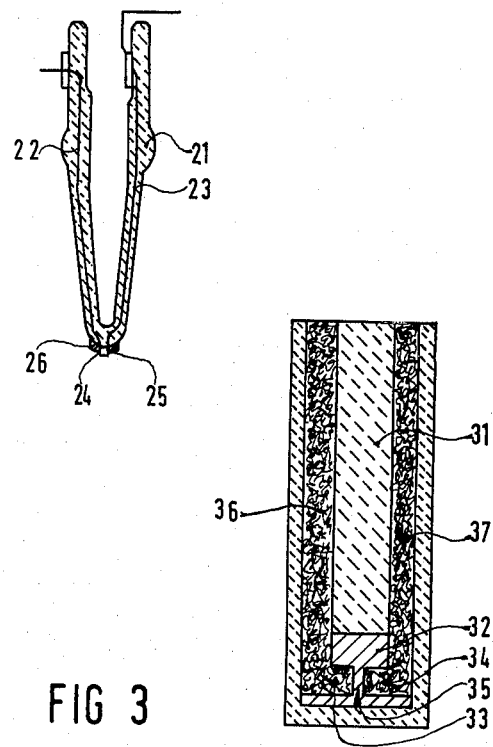
FIG 2
FIG 3

SELF-RECOVERING SOOT DETECTOR, PARTICULARLY TO MONITOR CARBON CONTENT IN DIESEL ENGINE EXHAUST GASES

The present invention relates to a sensor to determine free carbon or soot content in gases, and more particularly the soot content in the exhaust gases from Diesel engines.

BACKGROUND AND PRIOR ART

Incomplete combustion of heavy hydrocarbon compounds, such as heavy oils, Diesel oil, and the like leads to soot formation. In the operation of Diesel engines, which are increasingly used in automotive application, "smoking" of the engine leads to ambient air pollution although the carbon monoxide and hydrocarbon emission of the exhaust gases from the Diesel engine itself are very low. Thus, in spite of the high operating efficiency and low fuel consumption of Diesel engines, their use in automotive application has been held back due to emission of visible black exhaust from improperly operating or adjusted engines. It is, therefore, desirable to detect the formation of soot or unburned carbon particles in the exhaust of the engine and to provide an output signal which then can be used to indicate the presence of soot and further to be used as a sensing or control signal, for example in a control loop, to automatically adjust air, or the supply of fuel for complete combustion and to prevent excess carbon formation. It is possible to sense the transparency of output gases optically; such installations, however, are more suited to fixed locations, for example for smokestacks, and are not readily adaptable to automotive use, particularly in view of the rugged and highly variable ambient operating conditions to which they are objected, including wide swings in temperature, temperature gradients, shock, vibration, and the like. It would, therefore, be desirable to provide a sensor which changes a characteristic directly upon the formation of soot which can be deposited on a sensing element. In the past, soot deposits on a sensing plate have been used, which changes the electrical conductivity of a sensor by the formation of a carbon bridge between electrodes. Such sensors are not suitable for continuous indication of carbon content since sensing is not reversible, that is, after formation of a carbon bridge, the sensor cannot immediately or with suitable response speed sense the absence of further carbon formation since the bridge of soot formed between the electrode will remain and cannot be promptly and effectively removed.

THE INVENTION

It is an object to provide a soot or free-carbon sensor, particularly adapted for vehicular, that is mobile, and particularly automotive use, in which the presence of soot can be sensed and, upon termination of this presence, the sensor will respond accordingly, so that the sensor will continuously responsive, reversibly, to the soot content within the gases, typically Diesel engine exhaust gases, to which it is exposed.

Briefly, a support body of electrically insulating material is provided supporting two spaced electrodes, with an open gap therebetween, which are positioned to be in contact with the exhaust gases. A layer of electrically non-conductive material is located between the electrodes, the non-conductive material having the characteristics that, in the presence of oxygen, it catalyzes the oxidation of soot which will deposit thereon. Thus, if soot will deposit on the nonconductive catalyzing layer between the electrodes to form a soot bridge, a power source connected between the electrodes will have current flow occur therebetween, the extent of which can be measured to form an indication, sensing, or control signal. If, for example when the exhaust from a Diesel engine is sensed, the "smoking" condition ceases, so that excess oxygen is present, the catalytic support material for the electrodes will cause burn-off of the collected soot so that it will be removed by oxidation in the presence of the oxygen, thereby restoring the sensitivity of the sensor for subsequent detection of soot, that is, for the subsequent formation of a bridge of soot. The current flow between the electrodes then will be interrupted, thus providing an output signal representative of soot-free operation.

The sensor has the advantage that the output signal therefrom is continuously representative of actual smoking or smoke or soot content within the gases to which it is exposed. After termination of the formation of soot, the soot itself is oxidized at the portions where it forms bridges between the exposed electrodes, which bridges are removed and change the electrical characteristics of the sensor back to those which it had before the formation of the soot. The electrical resistance between the electrodes drops upon the initial formation of a soot bridge therebetween; after burn-off of soot, the resistance rises again by successive oxidation and removal of the soot which was deposited between the electrodes. The sensor can be constructed in extremely simple manner, thus can be inexpensively made, is rugged and suited for automotive application.

A suitable material for the catalytic layer or region between the electrodes includes platinum. This layer should be essentially non-conductive, so that the resistance between the electrodes is essentially determined by the soot therebetween. Thus, very small quantities of platinum added to a base or matrix material, or some other catalytically active noble metal, or noble metal alloys suffice. The upper limit of concentration of the catalytically active material is determined by undue drop in resistance of the material which separates the electrodes, that is, the appearance of electrically conductive continuous channels or paths between the electrodes. Aluminum oxide is a particularly suitable electrically insulating carrier or body or matrix; a mixture made of aluminum oxide and platinum provides an effective catalyzing, electrically non-conductive layer. Platinum is a suitable material for the electrodes themselves.

Drawings, Illustrating Various Examples

FIG. 1 is a transverse sectional view through a first embodiment of a sensor, and additionally showing the electrical connections thereto;

FIG. 2 is a highly schematic longitudinal view through a sensor particularly adapted for automotive applications and for insertion into an automotive-type socket similar to a spark plug socket, and omitting all electrical circuitry; and FIG. 3 is a front view of another embodiment of a sensor.

The sensor in accordance with FIG. 1 is a generally cylindrical pill-like disk of, for example, 7 mm diameter and 2 mm height. The material is aluminum oxide. The cylindrical surface 12 is coated with a layer 13 made of aluminum oxide and platinum, with a content of about 35% (by weight) of platinum. The parallel surfaces of the cylindrical body 11 have two electrodes 14, 15 applied thereto by thick-film technology, for example of about 0.02 mm thickness. They are made of a mixture of 95% platinum and 5% aluminum oxide (by weight). The electrodes 14, 15 extend around the facing surfaces and to the cylindrical outer surfaces over the layer 13 leaving, however, a gap between each other. This gap 16 has a width of about 0.1 mm, that is, a width which is large with respect to the thickness of the electrodes themselves (FIG. 1 shows the electrodes 14, 15, greatly enlarged for better visibility). The sensor is secured to a metal holder or socket which can place the sensor within the exhaust gas stream of an internal combustion engine using heavy oils, such as a Diesel engine. Suitable electrical connections are provided to a battery B through an indicator or sensing element which is shown schematically as a current meter or ammeter A. Terminals A1, A2 across the sensing element or meter can be used to take off a sensing or control signal for further processing. The signal taken off across terminals A1, A2 may, for example, be connected to a controller which controls the amount of fuel being supplied to a Diesel engine, or changing the pressure of fuel supply to the injection system. Electrode 14 is connected to the positive terminal of battery B, electrode 15 to the negative or chassis or reference terminal. The battery may, for example, be the usual battery of an automotive vehicle. The holder (not shown) is preferably so constructed that it can be screwed into a suitable tapped opening within the exhaust gas system of the engine, in such a manner that the sensor is exposed to the exhaust gases.

Operation

If the exhaust gases are free from soot, the gap 16 between the electrodes 14, 15 provides a high resistance path therebetween, and the indicator A will indicate only a very low or residual or quiescent current which can be sensed also at terminals A1, A2. Upon smoking of the engine, soot will be present in the exhaust gases which will deposit between the electrodes 14, 15 at the gap 16, forming a bridge of conductive carbon, which substantially lowers the electrical resistance between the electrodes 14, 15. Upon lowering of the resistance, current will flow through the meter A, and this current flow can be detected also as a signal taken off terminals A1, A2. The signal can then be processed, for example conducted to a threshold sensing or threshold detection circuit which, when the signal exceeds a certain threshold—indicative of a certain thickness of soot between the electrodes, and hence of a certain lowered resistance therebetween—the threshold circuit can then provide an output signal which controls a suitable fuel supply controller to change either the fuel or the quantity of air being supplied so that the fuel-air ratio which is appropriate for non-smoking, soot-free operation can be reestablished. The control should be so arranged that the region of fuel-air ratio which tends to form soot will be avoided, and preferably excess air or oxygen be supplied. Upon change of the fuel-air ratio, resulting in elimination of soot formation, the soot which had previously collected across the gap 16 will be oxidized at the catalytically active surface of the layer 13, and will flake or peel off from the gap 16, or be otherwise removed therefrom, for example by the flow of gases which, now, are soot-free, past the sensor. This causes the resistance between the electrodes 14, 15 to rise.

The advantage of the sensor in accordance with the present invention is, essentially, the reversibility of sensing, in that the sensor is capable of changing a characteristic—its resistance—which accurately reflects the actual condition of the gases to which it is exposed with comparatively high response speed, that is, with low time lag between actual change of conditions and indicated change by the sensor.

In principle, any arrangement of electrodes on the catalytically active layer 16 can be used, in which two exposed electrodes are connected by a catalytically active, but electrically effectively insulating layer. The entire region of first electrode—catalytically active surface—second electrode is exposed to the gas, the soot content of which is to be determined. FIGS. 2 and 3 show different embodiments, particularly suitable for automotive applications.

FIG. 2

The sensor consists of a ceramic tube 21 made of aluminum oxide, which is open at one end. Two platinum wires 22, 23 are included in the wall of the sensor, the platinum wires projecting beyond the closed end of the tube by a distance of about 0.1 mm. The projecting ends 24, 25 of the electrodes formed by the wires 22, 23 are embedded in a layer 26 of aluminum oxide in which 35% platinum (by weight) is included, the layer 26 having a thickness such that the electrode ends 24, 25 project therefrom by a tiny amount, and the electrodes are directly exposed to the exhaust gases. Upon smoking of the exhaust, a bridge of soot can form between the electrodes which leads to a decrease in the resistance therebetween. The electrical connection of the electrode wires 22, 23, and the operation of the sensor in accordance with this embodiment is identical in all respects to that described in connection with FIG. 1.

Embodiment of FIG. 3: A small plate 31 of aluminum oxide, for example of generally rectangular shape and having a width of 10 mm, a thickness of 1 mm, and a length of 50 mm, is held in a suitable holder, for example of the type usually used in connection with spark plugs. The length of the plate or disk 31 is determined by the length of the holder or socket in which the sensor is supported. One face of the disk 31 has a catalytically active layer 32 applied thereto, consisting of aluminum oxide and 35% by weight of platinum. Thick-film technology is appropriate for its application. Two electrodes 33, 34 are applied thereover, likewise in thick-film technology. The electrodes 33, 34 have a composition of 5% aluminum oxide and 95% platinum—by weight. The two electrodes are spaced from each other by a gap 35 of about 0.1 mm width. The electrodes 33, 34 are continued along the face of the plate or disk 31 in the form of conductive strips or paths 36, 37 to provide an electrical connection which preferably is made at the other end of the disk 31.

The operation and electrical connection of the sensor element of FIG. 3 is similar to that described above in connection with FIG. 1.

Introduction of the sensor elements into the gas stream, the soot content of which is to be determined, for example the exhaust from a Diesel engine, is preferably done by securing the sensor elements themselves in suitable sockets made of metal. The socket may, directly, form one terminal connection, for example the chassis or ground connection to the negative terminal of the battery. The other terminal is brought out to a connecting cap. Sockets used in general in connection with spark plugs, and shaped similarly thereto, and having spark plug-type threads, are suitable; other socket constructions, for example as used in connection with oxygen-exhaust gas sensors, also referred to as λ sensor, and of the type described, for example in U.S. Pat. Nos. 3,841,987, Friese et al, 3,960,692, Weil et al, both assigned to the assignee of the present application, are also suitable.

The layer 13 applied, for example, to surface 12 (FIG. 1) of the support body 11 is, preferably, a mixture made of a ceramic material and a catalytically active material, in which the ceramic material, preferably, is selected to be similar to and especially identical to the support material 11. The ceramic is preferably a metal oxide having a high melting point, and the catalytically active material is platinum, a platinum metal, or a platinum metal alloy, or an oxide of a transition metal such as $Cr_2O_3$, $SnO_2$ or $Fe_2O_3$, or a mixture of oxides of transition metals, such as $Cr_2O_3 \cdot (Fe_2O_3)_x$. In a preferred form, the catalyzing electrically essentially non-conductive layer is of aluminum oxide and platinum. The quantity of platinum therein will determine the conductivity, as well as the catalytic effectiveness; too little platinum will not provide sufficient catalytic action for oxidation of soot thereon after the soot formation in the exhaust gases has ceased; too much will lower the resistance of the layer. A content of from between 1 to 35%—by weight—platinum can be used, although, preferably, the platinum content of an aluminum oxide-platinum mixture for the layer 13 is preferably about 10 to 35% and most desirably 30 to 35% by weight.

The width of the gaps 16, 35, and of the gap between the electrode ends 24, 25 is not critical, and may vary widely, for example between 0.01 and 0.5 mm; a preferred range for the width of the gap is between 0.05 and 0.2 mm, with 0.1 mm being particularly suitable.

Various changes and modifications may be made, and features described in connection with any one of the embodiments may be used with any of the others, within the scope of the inventive concept.

The signal taken off the terminals A1, A2 (FIG. 1), forming a sensing signal representative of current flow through the sensor, can be processed in a closed fuel-air proportioning supply system, as well known in connection with the control of the fuel-air ratio of gasoline fuel injection systems for combination with Otto-type gasoline engines. A suitable control system, for example to control the quantity of air with respect to the quantity of fuel being supplied to a Diesel engine, is described in Appl. Ser. No. 816,844, assigned to the assignee of the present application, which system can be readily adapted to control the relative proportion of fuel and air supplied to a Diesel engine as well by substituting the sensor in accordance with the present application for the exhaust gas composition sensor there described, and suitably adapting the output of the control system to a Diesel engine, rather than an Otto-type engine. The meter A has been indicated, schematically, as an indicating instrument; it may, of course, be replaced by the emitter-base path, for example, of a transistor, to provide output signals across the collector-emitter thereof, then forming the terminals A1, A2 which, after suitable amplification, can be used to control the air-fuel control system referred to above.

The embodiment of FIG. 3 provides particularly good sensitivity in view of the large area of exposed catalytic surface of the layer 32, extending around both sides of the electrodes 33, 34, and spanning the gap 35, thus resulting in rapid oxidation of any soot which collects across the gap 35 upon the presence of oxygen, for example termination of "smoking" of a Diesel engine with which the sensor is used.

I claim:

1. System to determine smoking of a Diesel engine comprising
    a self-recovering soot detector to monitor the presence and absence of soot in the exhaust gases from the diesel engine, said soot detector including
    a support body (11, 21, 31) of electrically insulating material;
    two electrodes (14, 15; 24, 25; 33, 34) secured to the electrically insulating support body having end portions directly exposed to in contact with the exhaust gases spaced from each other by an open gap (16, 35) therebetween to provide for a resistance between said electrodes of essentially an open circuit and to detect the presence of soot upon smoking of the engine by the deposition of soot forming an electrically conductive bridge across said open gap and between the spaced, exposed end portions; a layer (13, 26, 32) of an electrically essentially non-conductive catalytically active material located on said support body in the region of said gap and directly exposed to said gases, said essentially non-conductive catalytically active material catalyzing, in the presence of oxygen, in the exhaust gases, upon non-smoking operation of the engine, the oxidation of soot present and deposited on the surface thereof and hence in the gap between said electrodes to remove soot precipated from the exhaust gases under smoking condition by catalytically activated oxidation of the soot to thereby restore essentially open circuit state between the electrodes and of the sensor for subsequent detection of accumulation of soot in said gap;
    means (A, B) determining change of resistance of the electrical path between said electrodes in operation of said engine as a measure of the deposit of carbon particles or soot in the gap between the electrodes and forming a conductive bridge therebetween upon the presence of soot;
    and means (A1, A2) deriving an output signal from said electrodes representative of and responsive to said change in resistance of the path between the electrodes between conduction and essentially non-conduction to permit control of the air-fuel supply to the engine in a direction to maintain the resistance between the electrodes at a high level.

2. Sensor according to claim 1, wherein said electrically non-conductive layer (13, 26, 32) having catalytic action comprises a mixture of ceramic material and a catalytically active material dispersed in the ceramic and having a concentration with respect to the ceramic within the range at which the layer remains essentially non-conductive.

3. Sensor according to claim 2, wherein the ceramic material of said mixture is a high-temperature melting metal oxide, and the catalytically active material comprises at least one of the materials selected from the group consisting of: platinum, a platinum metal, a platinum metal alloy, a transition metal oxide, $Cr_2O_3$, $SnO_2$ or $Fe_2O_3$, a mixture of transition metal oxides, $Cr_2O_3 \cdot (Fe_2O_3)_x$.

4. Sensor according to claim 2, wherein said layer of catalyzing electrically non-conductive material comprises aluminum oxide and platinum.

5. Sensor according to claim 4, wherein the layer comprises 1 to 35%—by weight—of platinum.

6. Sensor according to claim 1 or 2, wherein the gap (16) between the electrodes is between about 0.01 and 0.5 mm.

7. Sensor according to claim 1 or 2, wherein the gap (16, 35) between the electrodes is between 0.05 and 0.2 mm.

8. Sensor according to claim 1 or 2, wherein (FIG. 1) the support body (11) comprises a generally cylindrical disk-like element having a cylindrical surface (12);

the layer (13) of electrically non-conductive, catalyzing material being applied to said cylindrical surface and comprising a mixture of aluminum oxide and about 35%—by weight—of platinum;

and wherein the electrodes (14, 15) comprise cover layers which cover the major plane surfaces of the support body and extend over and around the layer (13) on the cylindrical surface, leaving a gap (16) between the electrodes in ring-form having a width of about 0.1 mm.

9. Sensor according to claim 1 or 2, wherein (FIG. 2) the support body (21) comprises a ceramic tube closed at one end of aluminum oxide; the electrodes comprise two platinum wires (22, 23) having end portions (24, 25) extending from the closed end of the ceramic tube by a short distance with a gap spacing between the electrodes of about 0.1 mm;

and said electrically non-conductive, catalytically active material comprises a layer (26) of aluminum oxide and about 35%—by weight—of platinum, surrounding the electrode ends (24, 25) and embedding the electrode ends while leaving said electrode ends exposed for contact with the exhaust gases.

10. Sensor according to claim 9, wherein said electrode ends (24, 25) project slightly beyond said layer (24, 25) of the electrically non-conductive, catalytically active material.

11. Sensor according to claim 1 or 2, wherein the support body comprises a plate (31) of aluminum oxide, said electrically non-conductive, catalytically active material comprising a layer of ceramic oxide and about 35% —by weight—platinum applied to a portion of a side of said plate;

and the electrodes (33, 34) comprise two layers of thick film formed of a mixture of platinum and a ceramic powder and applied to said plate and extending over said layer of electrically non-conductive, catalytically active material leaving said gap (35), said gap having a width of about 0.1 mm, the electrodes extending in the form of continuous conductive paths (36, 37) from the portion at which the electrically non-conductive, catalytically active layer (32) is applied towards another portion of said plate.

12. Sensor according to claim 11, wherein the ceramic powder with which the platinum to form the electrode is mixed comprises aluminum oxide powder.

13. Sensor according to claim 1, wherein the electrodes (14, 15) comprise a thick film layer formed of a mixture of a high melting point metal oxide ceramic material and a metal comprising platinum, a platinum alloy, a platinum metal alloy and present in a quantity sufficient to provide electrical conductivity to said mixture and continuous electrical paths therethrough.

14. Sensor according to claim 13, wherein the metal content of said mixture formng the electrode is at least about 50%—by weight.

* * * * *